(12) United States Patent
Cordova

(10) Patent No.: US 10,893,973 B1
(45) Date of Patent: Jan. 19, 2021

(54) OSTOMY BAG CLEANING APPARATUS

(71) Applicant: Jose Cordova, Ft Lauderdale, FL (US)

(72) Inventor: Jose Cordova, Ft Lauderdale, FL (US)

( * ) Notice: Subject to any disclaimer, the term of this patent is extended or adjusted under 35 U.S.C. 154(b) by 55 days.

(21) Appl. No.: 16/351,943

(22) Filed: Mar. 13, 2019

(51) Int. Cl.
| | | |
|---|---|---|
| *A61F 5/44* | (2006.01) | |
| *A61F 5/442* | (2006.01) | |
| *B08B 9/20* | (2006.01) | |
| *B67D 3/00* | (2006.01) | |
| *E03D 9/00* | (2006.01) | |

(52) U.S. Cl.
CPC ............ *A61F 5/442* (2013.01); *A61F 5/4405* (2013.01); *B08B 9/20* (2013.01); *B67D 3/0083* (2013.01); *E03D 9/00* (2013.01); *B08B 2209/085* (2013.01)

(58) Field of Classification Search
CPC .......... A61F 5/4405; A61F 5/442; B08B 9/20; B08B 2209/085; B67D 3/0083; E03D 9/00
USPC .......... 134/56 R, 57 R, 104.2, 166 C, 166 R; 604/332, 334, 335, 339
See application file for complete search history.

(56) References Cited

U.S. PATENT DOCUMENTS

| | | | |
|---|---|---|---|
| 5,503,633 A * | 4/1996 | Saunders | A61F 5/44 4/340 |
| 2006/0111682 A1* | 5/2006 | Schena | A61F 5/4407 604/334 |
| 2006/0237039 A1* | 10/2006 | Sarvis | B08B 9/08 134/22.1 |

* cited by examiner

*Primary Examiner* — Levon J Shahinian
(74) *Attorney, Agent, or Firm* — Sanchelima & Associates, P.A.; Christian Sanchelima; Jesus Sanchelima

(57) ABSTRACT

The present invention relates to an ostomy bag cleaning apparatus. The apparatus comprises support structure. The support structure comprises a support bar; a plurality of legs configured at one end of the support bar for supporting the support bar; and a mounting bracket fitted at an operative top end of the support bar. The apparatus further comprises a funnel supported at an operative top end of the support structure, wherein a user evacuates an ostomy bag, the funnel being mounted on the mounting bracket; a first conduit extending from the funnel, wherein the first conduit is a drain conduit for draining out the contents of ostomy bag; a second conduit routed into the funnel for allowing a user to wash the ostomy bag in the funnel; and a valve for regulating a supply of water to the second conduit.

10 Claims, 3 Drawing Sheets

OSTOMY BAG CLEANING APPARATUS

BACKGROUND OF THE INVENTION

1. Field of the Invention

The present disclosure relates to the field of ostomy bags. In particular, the present disclosure relates to an apparatus for allowing a user to conveniently clean their ostomy bags.

2. Description of the Related Art

An ostomy bag is a pouch that is attached to a user's body in the abdominal area subsequent to an ostomy operation in which portions of the intestinal or urinary tract are removed. The ostomy bag collect the waste products of the body via an opening formed in the abdominal area, typically referred to as a stoma. Cleaning of the ostomy bags has to be done daily, and the process of cleaning is typically laborious as it requires the user to take awkward positions while the cleaning is being done. This is not desired.

Several designs for ostomy bag cleaning devices and methods have been designed in the past. None of them, however, are known to be specifically designed to allows the user to wash the ostomy bag comfortably without having to assume awkward postures.

Applicant believes that a related reference corresponds to U.S. Pat. No. 5,503,633 filed by PHILIP K. SAUNDERS, LAWRENCE F. SHAFFER III, LAWRENCE F. SHAFFER IV, BURWELL R. EVANS, and MICHAEL W. MILLARD. The Saunders reference discloses an apparatus for the cleaning of an ostomy bag, wherein the apparatus provides a support for a patient at a sufficient height above a toilet bowl in the form of a platform having support bars with security stops and a chute removably hung from said platform to discharge excreta into the bowl. However, the apparatus disclosed in the Saunders reference fails to disclose any feature that allows the user to wash the ostomy bag comfortably without having to assume awkward postures, as can be seen in FIG. 3 of the Saunders reference.

Another related application is U.S. Patent Publication No. 20060111682 filed by KENNETH SCHENA and BLAINE SCHENA. The Schena reference discloses a closed drainage system for irrigating colostomy bags wherein the bag is irrigated and cleaned while in its operable position associated with the person. More specifically, the system mounts a manifold within the colostomy bag with an access to a water pressure from outside. However, the system disclosed in the Schena reference fails to disclose any feature that allows the user to wash the ostomy bag comfortably without having to assume awkward postures, as can be seen in FIG. 2 of the Schena reference, where the user is seated on the toilet seat backwards.

Other documents describing the closest subject matter provide for a number of more or less complicated features that fail to solve the problem in an efficient and economical way. None of these patents suggest the novel features of the present invention.

SUMMARY OF THE INVENTION

It is an object of the present invention to provide an ostomy bag cleaning apparatus that can be disposed just beside the commode so that the user can access the apparatus conveniently and with ease.

It is yet another object of the present invention to provide an ostomy bag cleaning apparatus using which the user does not have to remain in awkward positions while performing the cleaning of the ostomy bag.

Further objects of the invention will be brought out in the following part of the specification, wherein detailed description is for the purpose of fully disclosing the invention without placing any limitations thereon.

BRIEF DESCRIPTION OF THE DRAWING

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
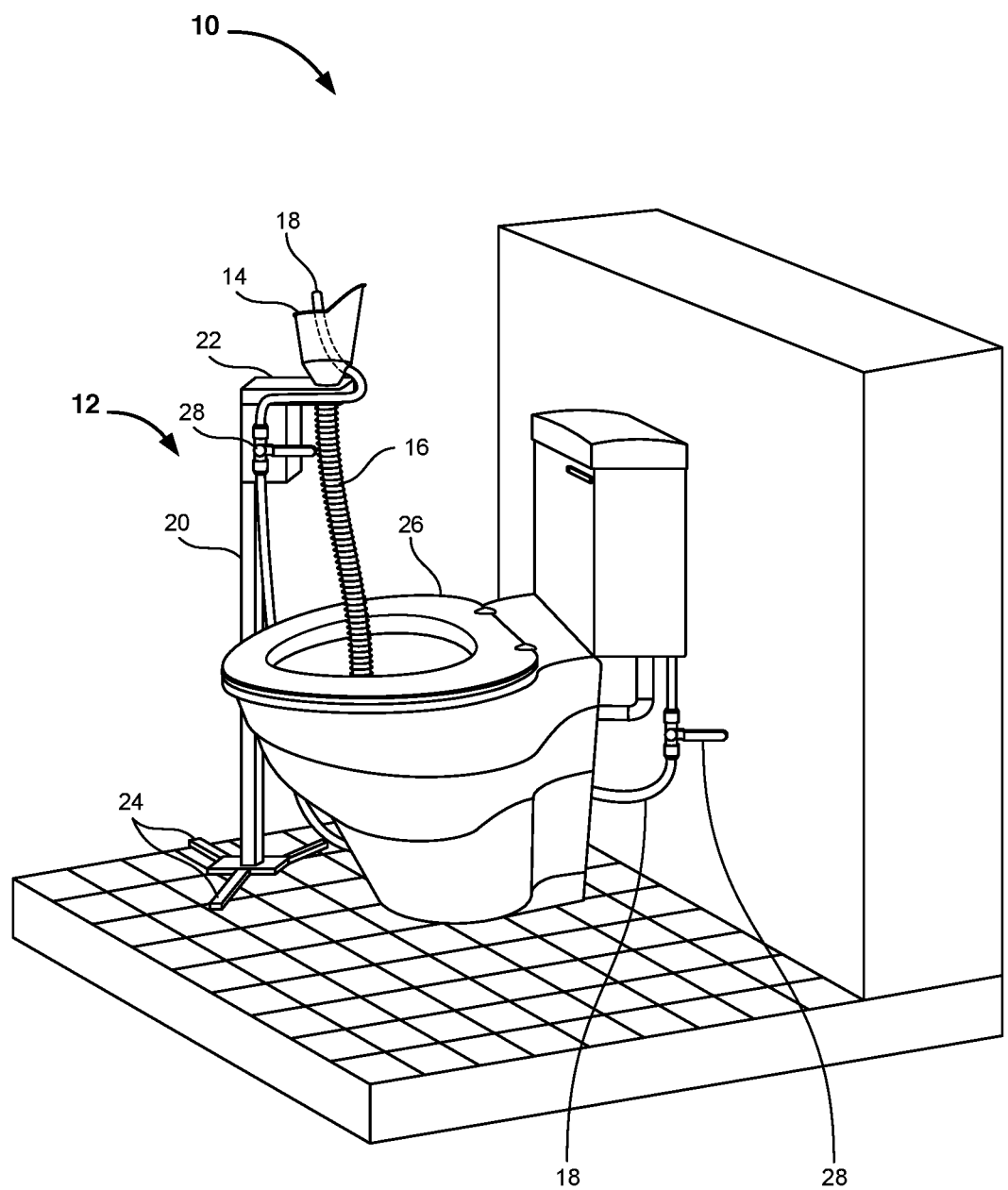
FIG. 1 illustrates a perspective view of an ostomy bag cleaning apparatus 10 (hereinafter referred to as apparatus 10), in accordance with an embodiment of the present invention, comprises a support structure 12, a funnel 14, a first conduit 16 extending from the funnel 14, and a second conduit 18 routed into the funnel 14 for allowing a user to wash the ostomy bag in the funnel 14.
Figure 2:
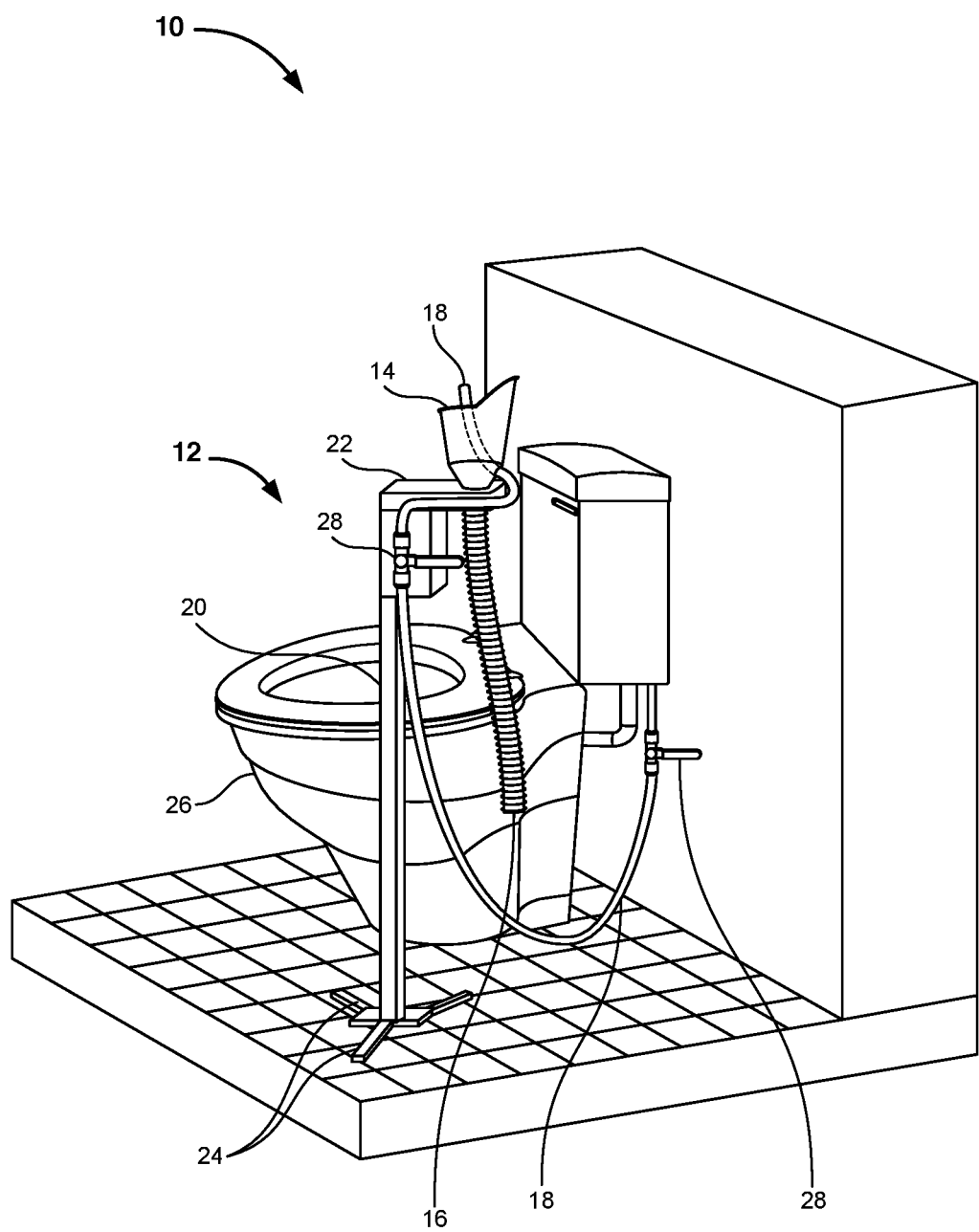
FIG. 2 illustrates another perspective view of the apparatus 10, in accordance with an embodiment of the present invention, wherein the apparatus 10 is inoperational and the first conduit 16 is outside a commode 26.

Referring now to FIG. 1 and FIG. 2, where the present invention is generally referred to with numeral 10, it can be observed that an ostomy bag cleaning apparatus 10 (hereinafter referred to as apparatus 10), in accordance with an embodiment of the present invention, comprises a support structure 12, a funnel 14, a first conduit 16 extending from the funnel 14, and a second conduit 18 routed into the funnel 14 for allowing a user to wash the ostomy bag in the funnel 14.

The apparatus 10 comprises the support structure 12. The support structure 12 is the structure that is supports the other elements of the apparatus 10 thereon. The support structure 12 comprises a support bar 20. On an operative top end of the support bar 20, a mounting bracket 22 is fitted. On the operative bottom end of the support bar 20, a plurality of legs 24 are provided for holding the support bar 20 in a substantially upright manner.

As seen in FIGS. 1 and 2, the support structure 12, along with the other components of the apparatus 10, is disposed adjacent a commode 26, in accordance with an embodiment of the present invention. Such a placement of the apparatus 10 allows the user to conveniently use the apparatus 10 while being seated on the toilet seat of the commode 26, without having to resort to awkward positioning of the body.

The apparatus 10 further comprises the funnel 14. The funnel 14 is fitted to the mounting bracket 14. The funnel 14 allows the user to wash ostomy bag therewithin. The apparatus 10 further comprises the first conduit 16 extending from the funnel 14. The first conduit 16 functions as a drain conduit for the funnel 14. The contents of the ostomy bag as well as the water used for washing the ostomy bag is drained via the first conduit 16 into the nearest drain point, which in accordance with an embodiment of the present invention, is the commode 26.

The apparatus 10 further comprises the second conduit 18. The second conduit 18 can be fluidly coupled to a water source. The apparatus 10 further comprises at least one valve 28 for regulating the supply of water to thru the second conduit 18. The second conduit 18 is wrapped around the support structure 12 and routed to the funnel 14. It is via the second conduit 18 that the user washes the ostomy bag within the funnel 14. In one embodiment, a dispersing attachment can be fitted at the free end of the second conduit 18 for efficiently distributing the water within the ostomy bag for cleaning the ostomy bag.

Figure 3:
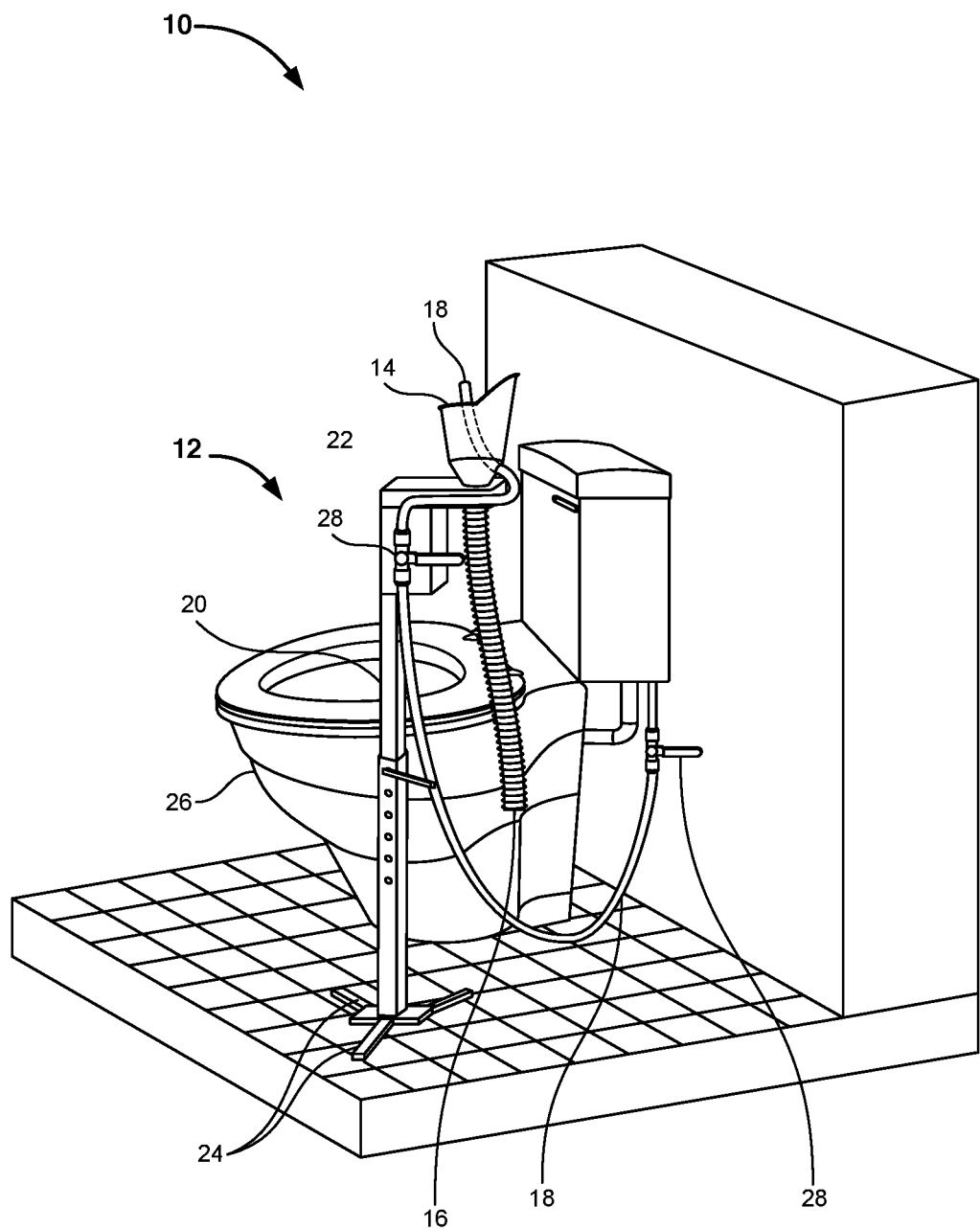
FIG. 3 illustrates another perspective view of the apparatus 10, in accordance with another embodiment of the present invention, wherein a support bar 20 of the support structure 12 has a telescopic configuration.

FIG. 3 illustrates another perspective view of the apparatus 10, in accordance with another embodiment of the present invention, wherein the support bar 20 of the support structure 12 has a telescopic configuration. The embodiments illustrated in FIGS. 2 and 3 are similar, with the only difference being that the support bar 20 has a telescopic configuration. As such, the embodiment 10 is not described again for the sake of brevity of the present disclosure.

The advantage of the apparatus 10, as disclosed in FIG. 3, is that a person in a wheelchair can just adjust the height of the support bar 20 so that they can use the apparatus 10 for cleaning their ostomy bags with relative ease and comfort.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An ostomy bag cleaning apparatus comprising:
   a. a support structure including a support bar, said support bar having a telescopic configuration;
   b. a funnel supported at an operative top end of the support structure, wherein a user evacuates an ostomy bag;
   c. a first conduit extending from the funnel, wherein the first conduit is a drain conduit for draining out the contents of ostomy bag; and
   d. a second conduit routed into the funnel for allowing a user to wash the ostomy bag in the funnel.

2. The apparatus according to claim 1, further comprising a valve for regulating a supply of water to the second conduit.

3. The apparatus according to claim 1, wherein a free end of the first conduit is open to a drain point.

4. The apparatus according to claim 3, wherein the drain point is a commode, and the apparatus is disposed beside the commode.

5. The apparatus according to claim 1, wherein the support structure comprises a plurality of legs configured at one end of the support bar for supporting the support bar.

6. The apparatus according to claim 1, wherein the support structure comprises a mounting bracket fitted at an operative top end of the support bar, wherein the funnel is mounted on the mounting bracket.

7. The apparatus according to claim 1, wherein the second conduit comprises a dispersing attachment for efficiently distributing the water within the ostomy bag for cleaning the ostomy bag.

8. An ostomy bag cleaning apparatus comprising:
   a. support structure including a support bar, a plurality of legs configured at one end of the support bar for supporting the support bar, a mounting bracket fitted at an operative top end of the support bar, said support bar having a telescopic configuration;
   b. a funnel supported at an operative top end of the support structure, wherein a user evacuates an ostomy bag, the funnel being mounted on the mounting bracket;
   c. a first conduit extending from the funnel, wherein the first conduit is a drain conduit for draining out the contents of ostomy bag;
   d. a second conduit routed into the funnel for allowing a user to wash the ostomy bag in the funnel; and
   e. a valve for regulating a supply of water to the second conduit.

9. The apparatus according to claim 8, wherein a free end of the first conduit is open to a drain point.

10. The apparatus according to claim 9, wherein the drain point is a commode, and the apparatus is disposed beside the commode.

* * * * *